United States Patent [19]

Usami et al.

[11] Patent Number: 4,736,618
[45] Date of Patent: Apr. 12, 1988

[54] SENSOR PROBE

[75] Inventors: Jun Usami, Nukata; Akinobu Hattori, Yokkaichi; Hiroshi Yamada, Nagoya, all of Japan

[73] Assignee: NGK Insulators, Ltd., Japan

[21] Appl. No.: 3,274

[22] Filed: Jan. 14, 1987

[30] Foreign Application Priority Data

Jan. 23, 1986 [JP] Japan .................. 61-12,741

[51] Int. Cl.⁴ .......................................... G01N 27/00
[52] U.S. Cl. .................................................. 73/23
[58] Field of Search ........................................ 73/23

[56] References Cited

U.S. PATENT DOCUMENTS 3,314,280  4/1967  Burns et al. ..................... 73/23
4,485,665  12/1984  Norman ........................ 73/23 X
4,609,875  9/1986  Jeffers ......................... 73/23 X

FOREIGN PATENT DOCUMENTS 3435874  4/1986  Fed. Rep. of Germany .......... 73/23

Primary Examiner—Stewart J. Levy
Assistant Examiner—Joseph W. Roskos
Attorney, Agent, or Firm—Parkhurst & Oliff

[57] ABSTRACT

The disclosed sensor probe for detecting a gas component concentration such as an oxygen concentration has a specific gas introducing tube arranged in a gas probe tube, whose one end is faced to a gas sensor portion, and possessing a gas inlet hole for introducing a gas to be measured into the gas sensor portion through the gas introducing tube and a gas outlet hole for discharging the gas. Under such a construction, since a sufficient amount of a gas to be measured can be supplied effectively into the gas sensor portion even if a velocity of the gas is low, it is possible to maintain a high measuring accuracy.

7 Claims, 1 Drawing Sheet

U.S. Patent
Apr. 12, 1988
4,736,618
FIG._1
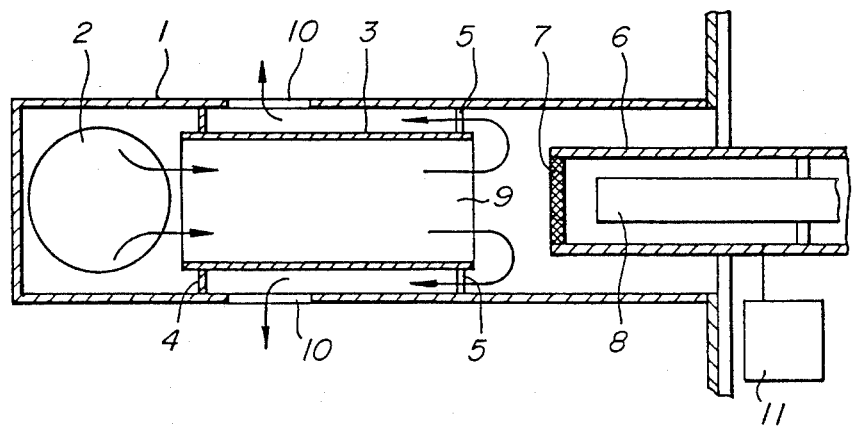
FIG._2
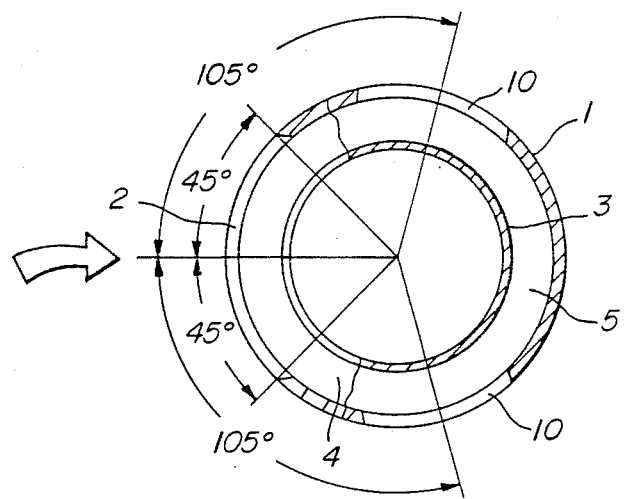

SENSOR PROBE

BACKGROUND OF THE INVENTION

1. Field of the Invention

The present invention relates to a sensor probe for measuring a gas which is introduced into a gas sensor portion.

2. Related Art Statement

As for a conventional sensor probe, there has been known, in the Japanese patent Laid-Open publication No. 123,759/85, a sensor probe wherein a tip portion of a pipe is cut out in a slantwise direction and a partition is arranged in a pipe longitudinal direction in such a manner that a tip of the partition is exposed from the cut out portion of the pipe. In the sensor probe mentioned above, the gas to be measured is introduced into the gas sensor portion arranged in the bottom of the pipe through a passage formed by the partition due to a gas pressure generated in the tip of the partition and then the gas is discharged through the other passage. In this case, if a gas velocity is less than 5 m/sec., a necessary amount of the gas to be measured cannot be introduced into the gas sensor portion, because the gas pressure generated in the tip of the partition is too low. Therefore, there occurs a drawback of an inaccurate measurement.

SUMMARY OF THE INVENTION

The present invention has for its object to eliminate the drawbacks mentioned above and to provide a sensor probe which can introduce a sufficient amount of the gas to be measured into the gas sensor portion even if the gas velocity is less than 5 m/sec. and which has a high measuring accuracy.

According to the invention, a sensor probe for detecting a gas component concentration such as an oxygen concentration having a gas probe tube and a gas sensor portion arranged near a bottom of said gas probe tube, comprises a gas inlet hole formed in a side wall of said gas probe tube at which a gas current is faced;

a gas introducing tube arranged in said gas probe tube, having a cross section substantially equal to that of said gas inlet hole, one end portion being faced to said gas sensor portion;

a partition for supporting said gas introducing tube with respect to said gas probe tube, used for isolating an outer surface of said gas introducing tube from a tip portion of said gas probe tube; and a gas outlet hole formed in the side wall of said gas probe tube at which the gas current is transverse, used for discharging the gas.

BRIEF DESCRIPTION OF THE DRAWINGS

FIG. 1 is a longitudinal cross sectional view showing one embodiment of the sensor probe according to the invention; and FIG. 2 is a transverse cross sectional view illustrating one embodiment of the sensor probe depicted in FIG. 1.

DESCRIPTION OF THE PREFERRED EMBODIMENTS

Hereinafter, embodiments according to the invention will be explained with reference to the drawings. In FIG. 1, a numeral 1 is a gas probe tube whose tip portion is closed, and a gas inlet hole 2 is formed in a tip side wall of the gas probe tube 1 at which a gas current shown in FIG. 2 by an arrow is faced. As shown in FIG. 2, it is preferable that the gas inlet hole 2 has an open angle of maximum ±45° with respect to a gas current direction. In this case, it is possible to introduce a sufficient amount of the gas to be measured into a gas sensor portion, even if the gas current direction is varied by about ±15°. Moreover, a numeral 3 is a gas introducing tube arranged in the gas probe tube 1, whose one end is faced to the gas inlet hole 2. The gas introducing tube 3 has a cross section substantially equal to that of the gas inlet hole 2, and is fixed in a central portion of the gas probe tube 1 by means of a partition 4 serving as a support plate and a support metal fitting 5. The partition 4 is used for isolating an outer surface of the gas introducing tube 3 from the tip portion of the gas probe tube 1. Since it is preferable to make an inner cross section of the gas introducing tube 3 substantially equal to an outer cross section thereof in the gas probe tube 1, it is preferable that the gas introducing tube 3 has a diameter of about 70 percent of an inner diameter of the gas probe tube 1.

Moreover, a numeral 6 is a gas sensor portion arranged in a bottom portion of the gas probe tube 1, and the gas sensor portion 6 is constructed by a filter 7 and a sensor 8. One end portion 9 of the gas introducing tube 3 is faced to the gas sensor portion 6. A distance between the end portion 9 and the filter 7 is set to a half to two times of the inner diameter of the gas introducing tube 3. Moreover, a numeral 10 is a gas outlet hole arranged in a side wall of the gas probe tube 1 at which the gas current is transverse. The gas outlet hole 10 is served to discharge a gas flowing through an outer space of the gas introducing tube 3. Further, as shown in FIG. 2, the gas outlet hole 10 is arranged at a position having an angle of 105°±15° with respect to the gas inlet hole 2. The number of the gas outlet hole 10 is not limited to one or a few, but it is preferable that a sum of the open area or areas is substantially equal to that of the gas inlet hole 2. Moreover, a numeral 11 is a gas supplier for supplying a reference gas into the gas sensor portion 6.

In an actual use, the sensor probe having the construction mentioned above is used under the condition that the gas inlet hole 2 arranged in the tip side wall of the gas probe tube 1 is faced to the current of the gas to be measured. Therefore, the gas to be measured is flowed into the gas probe tube 1 through the gas inlet hole 2, and is flowed through the inner portion of the gas introducing tube 3 having the cross section substantially equal to that of the gas inlet hole 2 into the gas sensor portion 6. In the gas sensor portion 6, for example, an oxygen concentration of the gas to be measured is detected. After that, the gas is discharged from the gas outlet hole 10 arranged in the side wall of the gas probe tube 1 through the outer space of the gas introducing tube 3.

In this manner, it is not different from the known sensor probe that the gas to be measured is introduced into the gas sensor portion 6 through the gas inlet hole 2 to detect, for example, the oxygen concentration and is discharged through the gas outlet hole 10. However, according to the invention, since the gas inlet hole 2 is arranged in the side wall of the gas probe tube 1 at which the gas current is faced so as to effect a gas supply from a position at which a gas pressure generated by an intrusion of the gas probe tube 1 into the gas current becomes highest, and the gas outlet hole 10 is arranged also in the side wall of the gas probe tube 1 at which the gas current is transverse and a negative pressure due to the gas current is generated, it is possible to introduce the gas to be measured effectively into the gas probe tube 1 by a pressure difference between a positive gas pressure near the gas inlet hole 2 and a negative gas pressure near the gas outlet hole 10. As a result, it is possible to supply a sufficient amount of the gas to be measured into the gas sensor portion 6 even if the velocity of the gas to be measured is about 1 m/sec. Therefore, the sensor probe according to the invention can maintain a high measuring accuracy even in velocity range of 1 to 5 m/sec. in which the measuring accuracy of the known sensor probe is decreased materially. Especially, if the gas outlet hole 10 is arranged in the gas probe tube 1 with the angle of 105°±15° with respect to the gas inlet hole 2, a portion near the gas inlet hole 2 is always maintained in a negative pressure state even if the direction of the gas current is varied by 15°, so that the measuring accuracy is not varied at all. Moreover, according to the invention, since the cross section of the gas introducing tube 3 is made substantially equal to that of the gas inlet hole 2, the gas to be measured can be flowed smoothly without generating a large pressure loss. Further, if a regulation plate is arranged in the gas probe tube 1 at a position opposite to the gas inlet hole 2, a gas attractive force can be increased materially.

As can be understood from the above, according to the invention, since a sufficient amount of the gas to be measured can be supplied effectively into the gas sensor portion even if the velocity of the gas to be measured is low, it is possible to maintain the high measuring accuracy. Therefore, the sensor probe according to the invention can obviate the conventional drawbacks, and can attribute to the improvement of the industry.

What is claimed is:

1. A sensor probe for detecting a gas component concentration having a gas probe tube for location directly within a gas current and a gas sensor portion arranged near one end of said gas probe tube, comprising:
   a gas inlet hole formed in a side wall of said gas probe tube facing an incoming gas current;
   a gas introducing tube arranged in said gas probe tube, having a cross sectional area substantially equal to that of said gas inlet hole, one end portion of said gas introducing tube facing said gas sensor portion;
   a partition for supporting said gas introducing tube within said gas probe tube and for isolating an outer surface of said gas introducing tube from a tip portion of said gas probe tube; and
   a gas oulet hole for discharging the gas, formed in the side wall of said gas probe tube at a position transverse to the direction of the gas current flow.

2. A sensor probe according to claim 1, wherein the edges of said gas inlet hole are at an angle of not greater than ±45° with respect to the gas current direction.

3. A sensor probe according to claim 2, wherein the gas current direction is at an angle of not more than ±15° with respect to the axis of the gas inlet hole.

4. The sensor probe according to claim 1, wherein the axis of said gas outlet hole is at a position having an angle of 105°±15° with respect to the axis of said gas inlet hole.

5. The sensor probe according to claim 1, wherein said gas introducing tube has an inner cross sectional area substantially equal to the cross sectional area defined between said gas introducing tube and said gas probe tube.

6. A sensor probe according to claim 1, wherein a distance between said one end portion of said gas introducing tube and said gas sensor portion is in the range of one half to two times an inner diameter of said gas introducing tube.

7. A sensor probe according to claim 1, wherein said gas sensor portion comprises an oxygen concentration sensor.

* * * * *